United States Patent
Brown et al.

(10) Patent No.: US 6,706,926 B1
(45) Date of Patent: Mar. 16, 2004

(54) DIPHOSPHINES

(75) Inventors: John Michael Brown, Oxford (GB); Duncan Carmichael, Oxford (GB); Henry Doucet, Oxford (GB)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 09/830,268

(22) PCT Filed: Oct. 29, 1999

(86) PCT No.: PCT/GB99/03599

§ 371 (c)(1),
(2), (4) Date: Oct. 9, 2001

(87) PCT Pub. No.: WO00/26220

PCT Pub. Date: May 11, 2000

(30) Foreign Application Priority Data

Oct. 29, 1998 (GB) .............................................. 9823716

(51) Int. Cl.[7] .................................................. C07F 9/50
(52) U.S. Cl. .......................................... 568/12; 568/13
(58) Field of Search ........................ 568/12, 13; 549/5, 549/6, 7, 216, 218; 548/111, 112; 546/21, 22

(56) References Cited

FOREIGN PATENT DOCUMENTS

| EP | 0 889 048 A | 1/1999 |
|---|---|---|
| GB | 1 466 803 | 3/1977 |
| GB | 1 501 558 | 2/1978 |
| GB | 1 501 559 | 2/1978 |
| GB | 1 501 599 | 2/1978 |
| GB | A-2 101 601 | 1/1983 |
| WO | WO 91/17998 | 11/1991 |
| WO | WO 98/02445 | 1/1998 |
| WO | WO 98/45040 | 10/1998 |
| WO | WO 99/24444 | 5/1999 |

OTHER PUBLICATIONS

J Am. Chem Soc by Imamoto et al 120 pp 1635–1636 Published on the Web Feb. 6, 1998.*
CA:73:99021 abs of J Chem Soc, C. by Hewertson (14) pp 1990–2 1970.*
CA:84:180349 abs of Zh. Obsch. Khim by Lutsenko 46(3) pp 568–71 1976.*
CA:130:252484 ab of JP11080179 by Wada et al Mar. 1999.*
CA:115:232482 abs of J Am. Chem. Soc. by Burk 113(22) pp 8518–8519.*
CA:125:86836 abs of Chem Ber. by Scherer et al 126(6) pp 697–713 1996.*
CA:115:208086 abs of J Organomet. Chem. By Brunner et al 413(1–3) pp 55–63 1991.*
CA:123:286190 abs of Z Naturforsch B Chem. Sci. by Heidel et al 50(5) pp 729–34 1995.*
Brunner et al., Journal of Organometallic Chemistry, (1991), 413, 55–63.
Ojima, Pure & Appl. Chem., (1984), 56, 99–110.
Burk et al., J. Am. Chem. Soc., (1998), 120, 4345–4353.
Ramsden et al., Tetrahedron Asymmetry, (1994), 5, 2033–2044.
Ramsden et al., J. Chem. Soc., Chem. Commun., (1995), 2469–2471.
Burk et al., Angew. Chem. Int. Ed., (1998), 37, 1931–1933.
Holz, J.: "Synthesis of a New Class of Functionalized Chiral Bisphospholane Ligands and the Application in Enantioselective Hydrogenations"; J. Org. Chem., vol. 63, No. 22, Oct. 8, 1998; pp. 8031–8034; XP–002130689.
Carmichael, D.: "HDybride P–chiral Disphosphines for Asymmetric Hydrogenation";, J. of Chem. Soc., Chem. Communications, No. 3; Feb. 7, 1999; pp. 261–262; XP–002130690.
Imamoto, T. et al., "P–Chiral Bis(Trialkylphosphine) Ligands and Their Use in Highly Enantioselective Hydrogenation Reactions"; J. Am. Chem. Soc., 1998, vol. 120, No. 7, Feb. 25, 1998; pp. 1635–1636; XP–000733409.
Burk, M.J.: "C2–Symmetric Bis(Phospholanes) and Their Use in Highly Enatioselective Hydrogenation Reactions"; J. Am. Chem. Soc., 1991, vol. 113, pp. 8518–8519; Jan. 1, 1991; XP–002065437.
Brunner, H.: "Asymmetric Calalyses XXXIII. New Optically Active Phospholanes Derived from Tartaric Acid"; J. of Organometallic Chemistry, Jul. 14, 1987; whole document; XP–002077949.
Imamoto, T.: "Synthesis and Reactions of Phosphine–Boranes"; J. of Am. Chem. Soc., 1990, vol. 112, No. 12, Jun. 20, 1990; whole document; XP–002130688.

* cited by examiner

Primary Examiner—Jean F. Vollano
(74) Attorney, Agent, or Firm—Quarles & Brady LLP

(57) ABSTRACT

A non-symmetrical diphosphine of the formula $R^1R^2P$—(Z)—$PR^3R^4$ wherein Z represents a chain of 2 to 4 carbon atoms which may be substituted, which chain may be saturated or unsaturated, and $R^1$, $R^2$, $R^3$ and $R^4$, which may be the same or differ, are aliphatic, aromatic or heteroaromatic groups attached to the phosphorus by carbon, nitrogen, oxygen or sulphur such that each phosphorus atom and its substituents independently form a single enantiomer.

9 Claims, 1 Drawing Sheet

DIPHOSPHINES

This application is a 371 of PCT/GB 99/03599 filed Oct. 29, 1999 now wo 00/26220.

The present invention relates to diphosphines, a process for their preparation, metal catalysts derived from them and the use of such catalysts.

There has been much interest in the asymmetric hydrogenation of alkenes in recent years using, in particular, rhodium catalysts derived from P-chiral diphosphines. There is a need to improve such processes so as to enhance the enantio-selectivity.

It is commonly believed that $C_2$ symmetric diphosphines along with diols and diamines are endowed with superior properties as ligands in catalysis and this is, of course, augmented by their ease of synthesis. According, to the present invention, we have surprisingly found that excellent results can be obtained by a novel class of unsymmetrical diphosphines.

Accordingly the present invention provides a non-symmetrical diphosphine of the formula

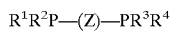

wherein Z represents a chain of 2 to 4 carbon atoms which may be substituted, which chain may be saturated or unsaturated, eg. ethylenically unsaturated, $R^1$, $R^2$, $R^3$ and $R^4$, which may be the same or different, are aliphatic, aromatic or heteroaromatic groups attached to the phosphorus by carbon, nitrogen, oxygen or sulphur such that each phosphorus atom and its substituents independently form a single enantiomer. It will be appreciated that, in general, there is a single stereochemical configuration around each phosphorus atom. Thus one or both phosphorus atoms may form a chiral centre. Suitable substituents of Z are hydrogen or aliphatic, aromatic or heteroaromatic groups.

Preferably the diphosphines are 1,2-ethanes ie. the carbon chain is —(CH$_2$)$_2$—. Other typical Z groups include those having the chain structure —C—C=C—C and —C—C=C—.

Generally, the substituents $R^1$, $R^2$, $R^3$ and $R^4$ will be connected to the phosphorus atoms by carbon atoms. In a preferred embodiment, $R^1$ and $R^2$ and/or $R^3$ and $R^4$ are linked together to form the substituted or unsubstituted 3,4,5,6 or 7 membered phosphorus heterocycle and preferably a phospholane ie. a five membered ring. This ring desirably has the formula

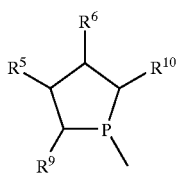

wherein $R^5$ and $R^6$, which may be the same or different, are hydrogen, hydroxy or $C_1$ to $C_4$ alkoxy and $R^9$ and $R^{10}$, which may be the same or different, are hydrogen or $C_1$ to $C_4$ alkyl.

It is also preferred that $R^1$, $R^2$, $R^3$ and/or $R^4$ are substituted or unsubstituted phenyl, the substituents preferably being hydroxy or $C_1$ to $C_4$ alkoxy groups.

The alkyl and alkoxy groups are typically methyl and methoxy, respectively.

It will be appreciated that although the diphosphines are non-symmetrical $R^1$, $R^2$, $R^3$ and $R^4$ may all be the same provided that the stereo orientation of $R^1$ and $R^2$ on the one hand, is different from that of $R^3$ and $R^4$. The values of $R^1$, $R^2$, $R^3$ and $R^4$ must be such that each phosphorus atom and its substituents independently form a single enantiomer.

Preferred diphosphines of the present invention have the formula

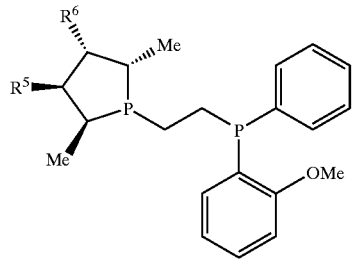

wherein $R^5$ and $R^6$, which may be the same or different, are hydrogen, hydroxy or $C_1$ to $C_4$ alkoxy.

In accordance with another aspect of the present invention these diphosphines can be obtained in optically pure form rather than as a mixture of isomers.

It is usually convenient if at least one of the phosphorus atoms is ligated to a borane. This enhances the storage stability of the phosphine. It will be appreciated that it is a simple matter to de-boronate when it is desired to generate the ligand. Catalysts can be obtained from the diphosphine with a, generally low valent, metal such as rhodium, iridium, ruthenium, palladium or platinum. The ligand can be reacted in known manner to generate the catalyst. For example a rhodium catalyst can be obtained by reaction of the ligand with $(COD)_2RhBF_4$. By "COD", as used herein, is meant cyclooctadiene. The preparation of the catalysts from the ligand can be obtained in known manner as one of skill in the art will appreciate.

The catalysts of the present invention are generally neutral or cationic complexes. Typical counterions which can be present if they are cationic include halide, for example fluoride or chloride, tetrafluoroborate, hexafluorophosphonate, hexafluoroantimonate, or sulphonate of formula $R^7SO_3$ where $R^7$ is an aliphatic or aromatic group, or boronate of the formula $(R^8)_4B$ wherein the $R^8$ groups which may be the same or different are aromatic groups. The aromatic groups are typically phenyl groups which are optionally substituted. When $R^7$ is aliphatic it is typically an alkyl group, for example of 1 to 4 carbon atoms such as methyl.

The non-symmetrical diphosphines of the present invention are generally prepared by a Michael-type addition reaction of a nucleophilic phosphorus-containing reactant with an unsaturated, preferably an ethylenically unsaturated, phosphorus-containing reactant or a cyclopropyl phosphorus-containing reactant.

The nucleophilic phosphorus-containing reactant may be any compound of the formula

wherein $R^{11}$ and $R^{12}$, which may be the same or different, are aliphatic, aromatic or heteroaromatic groups attached to the phosphorus bycarbon, nitrogen, oxygen or sulfur. The nucleophilic phosphorus-containing reactant may also be an organometallic derivative of the formula

which may be ionic or covalent, and in which $R^{11}$ and $R^{12}$ are as defined above and M is a suitable metal.

Preferably the nucleophilic phosphorus-containing reactant is an enantiomerically pure phosphine and most preferably it is an enantiomerically pure phosphine borane such as ortho-anisylphenylphosphine borane.

A phosphorus atom with electron-withdrawing substituents, attached to a double bond results in the alkene being responsive to nucleophiles. The unsaturated phosphorus-containing reactants suitable for use in the present invention may be oxidised phosphorus-bonded alkenes, for example diethyl vinylphosphonate, which may later be reduced to provide a primary phosphine. The alkene is preferably ethene or 1,3-butadiene.

The diphosphines of the present invention are typically prepared via a diphosphine intermediate comprising a primary phosphine and tertiary phosphine.

The primary phosphine may be elaborated by reaction with a doubly electrophilic carbon moiety which can provide a source of chirality giving an enantiomerically pure product. It may be converted into a phosphorus heterocycle by reaction with a diol activated by conversion of the hydroxyl groups into leaving groups. The diol may be activated by, for example, conversion into a halogen derivative, sulphate, sulfonate or phosphate. Diols suitable for use in the present invention include $C_2$ to $C_6$ diols. The diols may be unsaturated or saturated and they may optionally be substituted by oxygen, nitrogen, sulfur, aliphatic, aromatic or heteroaromatic groups.

It will be appreciated that other substituents may be attached to the primary phosphine in an analogous manner.

In the process of the present invention it is advantageous to convert one or both of the phosphorus atoms into, for example, oxide or sulfide derivatives, preferably borane derivatives, which may later be converted back into the desired phosphine or diphosphine.

DETAILED DESCRIPTION

Figure 1:
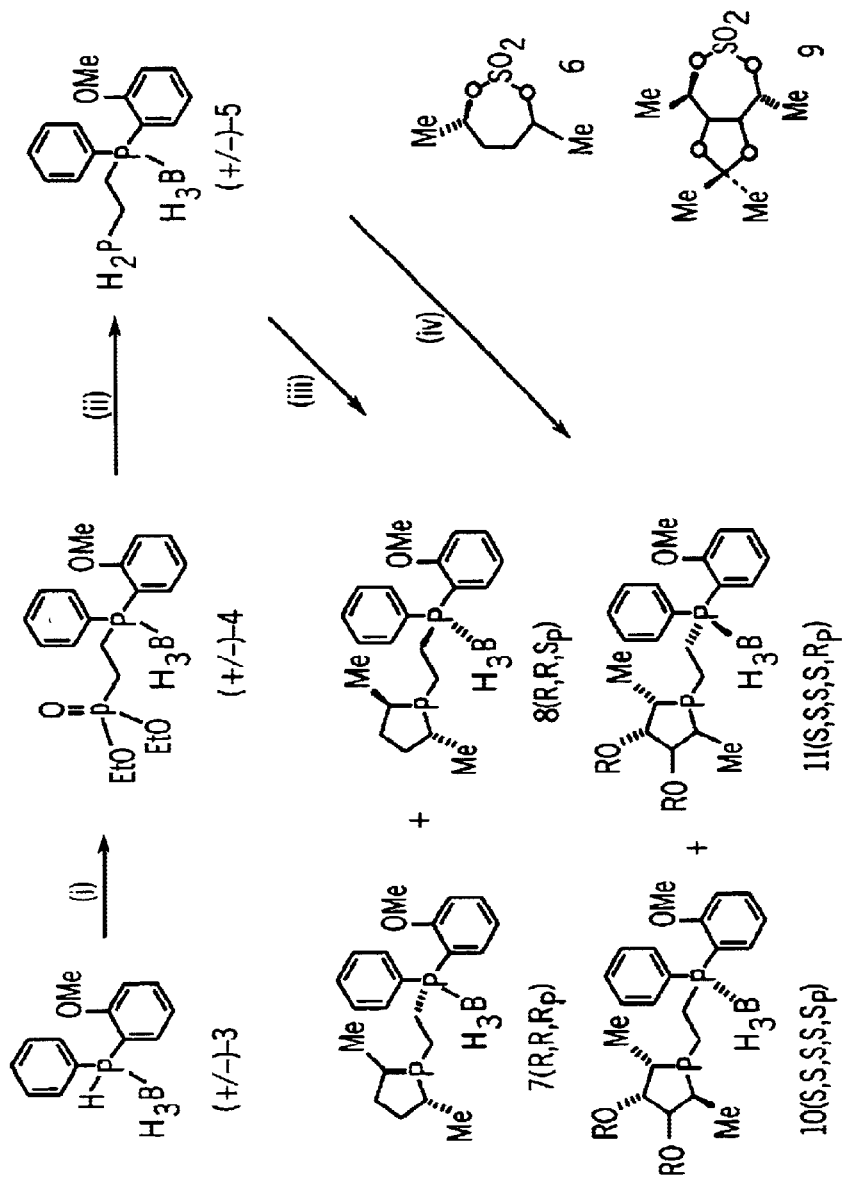
FIG. 1 shows an example of preparation of diphosphines according to the present invention.

An example of preparation of diphosphines according to the present invention is shown in Scheme 1 of FIG. 1. In Scheme 1 the diphosphines produced combine the phosphorus moieties of DIPAMP (R, R-1,2,-bis[(2-methoxyphenyl)phenylphosphino]ethane) 1 and BPE (1,2-bis[2,5-dialkyl phospholano]ethane) 2 are combined.

The synthesis shown in Scheme 1 of FIG. 1 is based on the conjugate addition of the racemic phosphineborane 3 to diethyl vinylphosphonate. Alane reduction of the product 4 gives the primary phosphineborane 5. Following deboronation, stepwise double nucleophilic displacement on the cyclic sulfate 6 via BuLi deprotonation gives the diphosphones 7 and 8 as a diastereomeric mixture. These compounds may be separated by MPLC (EtOAc/pentane). The analogous compounds 10-OH and 11-OH may be prepared from the mannitol derivative 9 as with a corresponding methyl ethers 10-OMe and 11-OMe.

The catalysts of the present invention may be used in the asymmetric catalytic conversion of a variety of compounds wherein a new C—B, C—Si, C—O, C—H, C—N or C—C bond is formed through the influence of the catalyst with control of the configuration at carbon. Such reactions include, for example, catalytic hydroboration, hydrosilylation, transfer hydrogenation, amination, cross-coupling, Heck olefination reactions, cyclopropanation, aziridination, allylic alkylation and cycloadditions. Preferably the catalysts are used in asymmetric hydrogenation. Preferred substrates for asymmetric hydrogenation include unsaturated esters such as esters of dehydroamino acids or methylenesuccinic acids. It has been found that using the catalysts of the present invention, a high enantiomer excess can be obtained from unsaturated esters under mild conditions. It is believed that a single site in the ligand directs reaction by H-bonding to the reactant and improves the enantio-selectivity.

The Examples which follow further illustrate the present invention.

EXAMPLES

The Synthesis of Enantiomerically Pure 1-(2-Methoxyphenylphenylphosphino)-2-(2,5-dimethyl-3,4-dimethoxyphospholanyl)ethane The cyclic sulfate precursor was prepared from the known mannitol-derived diol. (M Sanière, Y le Merrer, H El Hafa, J-C Depezay, F Rocchiccioli, *J. Labelled Cpd. Radiopharm.*, 1991, 29. 305.) Each compound may be obtained on ca 5 g scales as a crystalline solid. The cyclic sulphate 9 is preferably subjected to short-column chromatography, to remove traces of an impurity suspected to be the monofunctionalised sulphate (itself isolated and characterised by nmr). Nonetheless, it can be purified by crystallisation from ether-pentane. No acid-induced cleavage of the isopropylidene protecting group appears to take place.

Racemic o-anisylphenylphosphine and its corresponding borane complex were prepared without difficulty by the method of Imamoto. (T Imamoto, T Oshiki, T Onozawa, T Katsumoto and K Sato, *J. Am Chem. Soc.*, 112, 5244, 1990.) No scale-up problems were encountered and the reaction was adapted to give 40 g of product without difficulty. Both PhArPH and PhArPH($BH_3$) (Ar=phenyl, o-anisyl) smoothly underwent KOtBu-catalysed Michael addition to diethyl vinylphosphonate. Racemic 2-anisyl-phenylphosphinoethyl diethylphosphinoethyl phosphonate 4 and 2-diarylphosphinoethyl diethylphosphonate were obtained as their borane complexes on a 10 g scale in five minutes at room temperature. Alane reduction of this product gave the primary phosphine 5.

The cyclisation to diphosphines 10-OH and 11-OH was carried out by a two-stage sequence with butyl lithium in THF. Direct hydrolysis of the crude phosphine (TMSCI-MeOH) gave the diastereomeric diols which, running much more slowly on silica in pure ether than the impurities, were easily separated by column chromatography. The faster-running diastereomer (11-OH rf=0.25) can easily be obtained in enantiomeric excesses better than 99%.

Hydrogenation of Esters of Deliydroamino Acids or Methylenesuccinic Acid 2 ml of degassed dichloromethane was added to (0.105 mmol) of diphosphine borane under argon. 1.05 mmol of $HBF_4$ was added then the solution was stirred at 20–25° C. during 14 hours. Then 41 mg (0.1 mmol) of [Rh(COD)2]$BF_4$ was added. After being stirred for 10 minutes, the solvent was removed in vacuo and the yellow-orange residue was triturated three times with 5 ml of diethyl ether. The ether was removed via cannula filtration or syringe and the orange residue dried in vacuo. These complexes were stored in Schlenk tubes under argon. For the catalytic hydrogenation reactions the complexes were prepared just before use. 1 ml of a solution of Rhodium complex (2 mmol/l) in methanol was transferred under argon via cannula or syringe to a Schlenk tube under argon or hydrogen containing 0.2 mmol of olefin. The solution was placed under hydrogen and stirred at 20–50° C. during 2–5 hours. After evaporation of the solvent, the product was purified by chromatography on silica (methanol/dichloromethane). Enantiomeric excesses determined by NMR using Eu(hfc)$_3$ as chiral shift reagent or by gas chromatography using a column Chrompack WCOT Fused Silica, CP-Chirasil-DEX CB, 25 meters, inlet pressure 8 psi.

The hydrogenation of dehydroamino acids of different structures is shown in Table 1. From this it will be seen that the configuration of the phosphine and of the phospholane can be "matched" or "mismatched" according to their relative configurations. For the matched cases 11-OH and 11-OMe, enantiomer excesses of up to 92% can be obtained. It will also be seen that the extent to which the two centres influence the course of catalysis may differ greatly depending on the substrate.

TABLE 1

| substrate | ligand | e.e. |
|---|---|---|
| 12 | 10-OMe | 19 S |
|  | 11-OMe | 85 S |
|  | 10-OH | 43 S |
|  | 11-OH | 92 S |
|  | 7 | 60 R |
|  | 8 | 38 S |
| 13 | 10-OMe | 58 S |
|  | 11-OMe | 67 S |
|  | 10-OH | 82 S |
|  | 11-OH | 88 S |
|  | 7 | 5 R |
|  | 8 | 36 R |
| 14 | 11OMe | 77 S |
|  | 10-OH | 72 S |
|  | 11-OH | 90 S* |

Conditions: substrate:catalyst: 100:1, (COD)$_2$Rh BF$_4$ as precursor, 1.3 bar, MeOH, 1–3 h.
*OSO$_2$CF$_3^-$ instead of BF$_4^-$ The results of hydrogenation of itaconate esters and half-esters are shown in Table 2. The mismatched diastereomers of ligand 10 gave poor e.e.s and are not included. For the 1-substuted monoester 15, the hydroxy-ligand 11-OH gives a superior e.e. to its methyl ether. The reverse is true for the 4-substituted monoester 16, where the methyl ether 11-OMe provides the product of higher enantioselectivity.

TABLE 2

| substrate | ligand | e.e. |
|---|---|---|
| 15 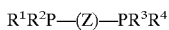 | 11-OMe | 85 R |
|  | 8-OH | 95 R |
| 16 | 11-OMe | 93 R* |
|  | 11-OH | 87 R |
| 17 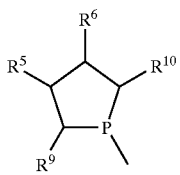 | 8-OMe | 85 R |
|  | 8-OH | 80 R* |

Conditions: substrate: catalyst: 100:1, (COD)$_2$Rh BF$_4$ as precursor, 1.3 bar, MeOH, 1–3 h.
*: 94% e.e. with OSO$_2$CF$_3^-$ instead of BF$_4^-$ These preliminary results indicate that, contrary to expectation, the enantioselectivity may be sensitive to a remote substituent in the phospholane ring. Inspection of molecular models suggests that the MeO— or HO— groups are axial in the 5-membered ring of the phospholane, and in the vicinity of substituents on the coordinated alkene. Hence cooperative association between ligand and substrate may exist through hydrogen-bonding.

What is claimed is:

1. A non-symmetrical diphosphine of the formula $$R^1R^2P\text{—}(Z)\text{—}PR^3R^4$$

said diphosphine not having C$_2$ symmetry, wherein Z represents a chain of 2 to 4 carbon atoms which may be substituted, which chain may be saturated or unsaturated, R$^1$, R$^2$, R$^3$ and R$^4$ each independently are aliphatic, aromatic or heteroaromatic groups attached to the phosphorus by carbon such that each of the moieties R$^1$R$^2$P and PR$^3$R$^4$ contains a chiral centre, and R$^1$ and R$^2$ are linked to form a substituted or unsubstituted 3, 4, 5, 6 or 7 membered phosphorus heterocycle.

2. A diphosphine according to claim 1, wherein Z represents a chain of 2 carbon atoms.

3. A diphosphine according to claim 1, wherein R$^1$ and R$^2$ are linked to form a ring of the formula:

wherein R$^5$ and R$^6$, which may be the same or different, are hydrogen, hydroxy or C$_1$ to C$_4$ alkoxy and R$^9$ and R$^{10}$, which may be the same or different, are hydrogen or C$_1$ to C$_4$ alkyl, and all of R$^5$, R$^6$, R$^9$ and R$^{10}$ cannot be hydrogen at the same time.

4. A diphosphine according to claim 1, wherein at least one of R$^3$ and R$^4$ is substituted or unsubstituted phenyl.

5. A diphosphine according to claim 4, wherein the phenyl group is substituted by one or more hydroxy groups.

6. A diphosphine according to claim 4, wherein the phenyl group is substituted by one or more or C$_1$ to C$_4$ alkoxy groups.

7. A diphosphine according to claim 1, wherein $R^3$ and $R^4$ are linked to form a substituted or unsubstituted 3, 4, 5, 6 or 7 membered phosphorus heterocycle.

8. A diphosphine according to claim 7, wherein $R^3$ and $R^4$ are linked to form a ring of the formula:

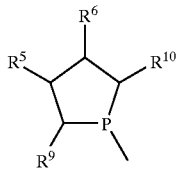

wherein $R^5$ and $R^6$, whichs may be the same or different, are hydrogen, hydroxy or $C_1$ to $C_4$ alkoxy and $R^9$ and $R^{10}$, which may be the same or different, are hydrogen or $C_1$ to $C_4$ alkyl, and all of $R^5$, $R^6$, $R^9$ and $R^{10}$ cannot be hydrogen at the same time.

9. A diphosphine of the formula

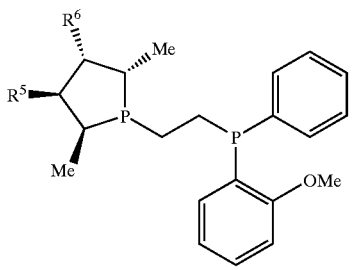

wherein $R^5$ and $R^6$, which may be the same or different, are hydrogen, hydroxy or $C_1$ to $C_4$ alkoxy, in the form of an optically pure isomer or a mixture of isomers.

* * * * *

UNITED STATES PATENT AND TRADEMARK OFFICE
CERTIFICATE OF CORRECTION

PATENT NO. : 6,706,926 B1
DATED : March 16, 2004
INVENTOR(S) : John M. Brown et al.

It is certified that error appears in the above-identified patent and that said Letters Patent is hereby corrected as shown below:

Title page,
Item [57], ABSTRACT,
Line 5, "differ" should read -- different --.

Column 3,
Lines 53-54, "diphosphones" should read -- diphosphines --.

Column 7,
Line 15, "whichs" should read -- which --.

Signed and Sealed this

Twenty-eighth Day of September, 2004

JON W. DUDAS
*Director of the United States Patent and Trademark Office*